US011701147B2

(12) United States Patent
Vordemvenne et al.

(10) Patent No.: US 11,701,147 B2
(45) Date of Patent: Jul. 18, 2023

(54) BONE ANCHOR FOR TRIANGULAR ILIOSACRAL OSTEOSYNTHESIS

(71) Applicant: Silony Medical International AG, Frauenfeld (CH)

(72) Inventors: Thomas Vordemvenne, Muenster (DE); Christoph Josten, Leipzig (DE); Frank Kandziora, Roedermark (DE)

(73) Assignee: Silony Medical International AG, Frauenfeld (CH)

( * ) Notice: Subject to any disclaimer, the term of this patent is extended or adjusted under 35 U.S.C. 154(b) by 792 days.

(21) Appl. No.: 16/633,265

(22) PCT Filed: Jul. 25, 2018

(86) PCT No.: PCT/EP2018/070162
§ 371 (c)(1),
(2) Date: Jan. 23, 2020

(87) PCT Pub. No.: WO2019/020690
PCT Pub. Date: Jan. 31, 2019

(65) Prior Publication Data
US 2021/0128203 A1 May 6, 2021

(30) Foreign Application Priority Data
Jul. 25, 2017 (DE) ...................... 10 2017 116 755.2

(51) Int. Cl.
*A61B 17/88* (2006.01)
*A61B 17/70* (2006.01)
(Continued)

(52) U.S. Cl.
CPC ...... *A61B 17/7055* (2013.01); *A61B 17/1757* (2013.01); *A61B 17/7082* (2013.01);
(Continued)

(58) Field of Classification Search
CPC ............ A61B 17/7055; A61B 17/1757; A61B 17/7082; A61B 17/863; A61B 17/8685; A61B 2017/8655
(Continued)

(56) References Cited

U.S. PATENT DOCUMENTS 6,053,916 A * 4/2000 Moore ................ A61F 2/30988
606/86 R
9,149,286 B1 * 10/2015 Greenhalgh ....... A61B 17/1757
(Continued)

FOREIGN PATENT DOCUMENTS

DE 10115014 A1 10/2002
DE 102007051136 A1 4/2009
(Continued)

OTHER PUBLICATIONS

German Examination Report, dated Feb. 19, 2018. pp. 1-10.
(Continued)

*Primary Examiner* — Eduardo C Robert
*Assistant Examiner* — David C Comstock
(74) *Attorney, Agent, or Firm* — George McGuire

(57) ABSTRACT

The invention relates to a bone anchor for triangular iliosacral osteosynthesis. The bone anchor includes an ilium screw having a first longitudinal direction and an iliosacral screw having a second longitudinal direction. The ilium screw, in a thread-free portion, has a preferably elongated-hole-like through-opening transversely to the first longitudinal direction, and the iliosacral screw has such a smaller outer diameter in relation to the ilium screw that the iliosacral screw can be guided through the through-opening and can be screwed proceeding from the ilium into the sacrum, through the ilium screw.

36 Claims, 13 Drawing Sheets

(51) Int. Cl.
*A61B 17/17* (2006.01)
*A61B 17/86* (2006.01)

(52) U.S. Cl.
CPC ........ *A61B 17/863* (2013.01); *A61B 17/8685* (2013.01); *A61B 2017/8655* (2013.01)

(58) Field of Classification Search
USPC ............ 606/279, 64–66, 301, 304–308, 310, 606/314–319, 321, 328, 96, 98, 102, 103, 606/104, 86 A
See application file for complete search history.

(56) References Cited

U.S. PATENT DOCUMENTS

| | | |
|---|---|---|
| 2010/0179550 A1 | 7/2010 | Schreiber et al. |
| 2014/0135850 A1 | 5/2014 | Parent et al. |
| 2015/0150683 A1* | 6/2015 | Donner .................. A61B 17/58 623/16.11 |
| 2015/0190187 A1 | 7/2015 | Parent et al. |
| 2016/0128732 A1* | 5/2016 | Strnad ................ A61B 17/7034 606/267 |
| 2016/0310188 A1 | 10/2016 | Marino et al. |
| 2018/0028246 A1* | 2/2018 | Kang .................. A61B 17/8685 |
| 2018/0303530 A1* | 10/2018 | Kang .................. A61B 17/8605 |
| 2018/0360512 A1* | 12/2018 | Mari .................. A61B 17/8695 |
| 2019/0083271 A1* | 3/2019 | Donner .............. A61B 17/1739 |
| 2019/0231405 A1* | 8/2019 | Redmond .......... A61B 17/8625 |

FOREIGN PATENT DOCUMENTS

| | | |
|---|---|---|
| WO | 2011014135 A2 | 2/2011 |
| WO | 2013000071 A1 | 1/2013 |

OTHER PUBLICATIONS

International Search Report and Non-Translated Written Opinion Form PCT/IS/210 and PCT/ISA/237, International Application No. PCT/EP2018/070162, pp. 1-9, International Filing Date Jul. 25, 2018, dated Nov. 20, 2018.

* cited by examiner

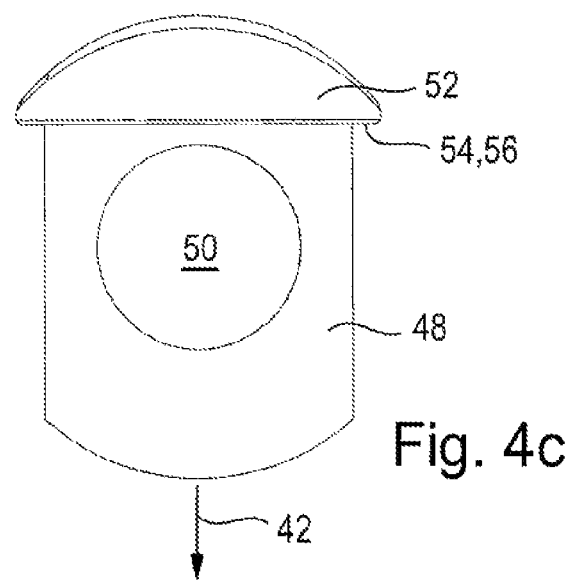

BONE ANCHOR FOR TRIANGULAR ILIOSACRAL OSTEOSYNTHESIS

CROSS-REFERENCES TO RELATED APPLICATIONS

This application is a national stage application under 35 U.S.C. 371 based on international patent application PCT/EP2018/070162 filed on Jul. 25, 2018, which claims priority to German Patent Application No. 10 2017 116 755.2 filed on Jul. 25, 2017, disclosures of both of which are incorporated herein by reference in their entireties.

BACKGROUND

The invention relates to a bone anchor for triangular iliosacral osteosynthesis, comprising an ilium screw having a first longitudinal direction and an iliosacral screw having a second longitudinal direction.

From US 2014/0135850 A1, such a bone anchor is known, wherein the ilium screw is passed through a slot-shaped opening in the iliosacral screw. However, this means a practical limitation for the outer diameter of the ilium screw or the iliosacral screw must be configured with a possibly oversized large diameter, which in turn brings disadvantages.

SUMMARY OF THE INVENTION

The object of the present invention is to provide a bone anchor for triangular iliosacral osteosynthesis, in which a fracture of the sacrum can be treated in an improved way, which also includes a favorable implantability of the bone anchor.

This object is achieved by a bone anchor of the type mentioned above, wherein the ilium screw in a thread-free portion has a preferably slot-shaped through-opening transverse to the first longitudinal direction, wherein the ilium screw, in a thread-free portion, has a preferably elongated-hole-like through-opening transversely to the first longitudinal direction, and the iliosacral screw has such a smaller outer diameter in relation to the ilium screw that the iliosacral screw can be guided through said through-opening and can be screwed proceeding from the ilium into the sacrum, through the ilium screw, wherein the ilium screw has a distal threaded portion having a distal core diameter and a nominal distal diameter of the thread and a proximal threaded portion having a proximal core diameter and a proximal nominal diameter of the thread, and wherein the thread-free portion between the proximal nominal diameter is greater than an outer diameter of the thread-free portion and the outer diameter of the thread-free portion is greater than the distal nominal diameter, and wherein a sleeve element having a shape complementary to the shape of the through-opening and made of a polymer material is inserted into the through-opening and is then held in the through-opening frictionally and additionally in a form-fitting manner relative to at least one direction, wherein the inner dimension of the sleeve element orthogonally to the first longitudinal direction is smaller than a nominal diameter of a thread of the iliosacral screw.

Due to the fact that the particular slot-shaped through-opening is formed in the ilium screw, i.e. the iliosacral screw is passed through this through-opening in the ilium screw, it is readily possible to form the iliosacral screw with a diameter of only 6 mm-9 mm maximum, which is advantageous for the applications. This further means that the outer diameter of the ilium screw, at least in the region of the through-opening, must be dimensioned so that the through-opening can have the required size for the iliosacral screw. This proves to be less problematic, since the ilium screw is placed in a region of the ilium, where the anatomical characteristic of the ilium and in particular the bone strength of the ilium allows said placing.

Furthermore, a good and stable fixation of the iliosacral screw with respect to the ilium screw can be achieved by the sleeve element made of polymer material inserted into the through-opening. Furthermore, according to the invention, since the sleeve element is form-fittingly held in the through-opening in the pressed-in state not only frictionally, but additionally at least in one direction, that is, with respect to the press-in direction or the opposite direction, it is possible to safely prevent the sleeve element from leaving its intended position in the through-opening, in particular during screwing of the iliosacral screw, when the iliosacral screw cuts with its thread into the material of the sleeve element. If such a form-fit engagement is realized only in one direction, which is sufficient, it proves to be advantageous if the form-fit engagement is oriented with respect to this one direction in such a way that when screwing the iliosacral screw the sleeve element is not stressed in the release direction but rather in the direction of form-fit engagement. Here, the surgeon should therefore make sure that the ilium screw is oriented with its inserted sleeve element in the appropriate rotational position when inserting the iliosacral screw. In contrast, this orientation is not important in the case of a form-fit engagement in the press-in direction and counter to the press-in direction.

It proves to be advantageous if the sleeve element consists of a polymer material that is dimensionally stable, but slightly yieldable deformable, in particular elastically deformable, such that it can be slightly oversized with respect to the through-opening and can then be pressed with slight deformation into the through-opening.

The sleeve element is preferably formed of polyethylene, in particular of ultra-high molecular weight polyethylene (UHMW PE), PEEK, PEAK, PEKK, PPSU or PPS. Preferably, non-crosslinked polyethylene is used, which does not tend to be brittle.

Furthermore, it proves to be advantageous that an inner dimension of the through-opening orthogonally to the first longitudinal direction is at least 6.0 mm, in particular at least 7.0 mm and more particularly at most 11.5 mm, in particular at most 10.5 mm, in particular at most 9.5 mm.

It is further proposed that an inner dimension of the sleeve element orthogonal to the first longitudinal direction is smaller than a core diameter of a thread of the iliosacral screw. In this way, excessive displacement or plastic deformation of the material of the sleeve element can be avoided by merely cutting the threads of the iliosacral screw, without cutting its core into the sleeve element or displacing the material thereof.

As already indicated, it proves to be advantageous that a nominal diameter of a thread of the iliosacral screw is at least 6 mm and at most 9.5 mm, in particular at most 8.5 mm.

For the formation of the sleeve element, it is further proposed that the sleeve element has a wall thickness of at least 1.0 mm, in particular of at least 1.5 mm and at most 3.5 mm, in particular of at most 3.0 mm, in particular of at most 2.5 mm.

In order to realize the form-fitting acting engagement with respect to the press-in direction or possibly with respect to the opposite direction, it would be possible for the opening in the press-in direction or in the opposite direction to be tapered in a suitable manner, in particular to form conical or wedge-shaped boundary surfaces, wherein the sleeve element would preferably be formed in a complementary manner. According to a further embodiment of the invention, it is proposed that the sleeve element has at least one projection projecting transversely to its press-in direction, by means of which a form-fitting engagement of the sleeve element with the ilium screw is achieved. This projection can then run against a particular correspondingly complementary abutment point on the ilium screw, whereby the form-fit engagement can be realized.

In a further development of this idea, it proves to be advantageous if the projection forms a step on the sleeve element. This projection or step is further preferably extended in a circumferential direction of the sleeve element. The projection or the step can form a flange on the sleeve element which is broken in the circumferential direction or continuous in the circumferential direction. In this embodiment, the sleeve element can be supported evenly over its circumference in the inserted state, whereby the form-fit engagement then also uniformly supports the sleeve element over the circumference, provided that forces are introduced to the sleeve element, in particular when screwing the iliosacral screw.

Furthermore, it proves to be advantageous that the through-opening is formed with a recess or step which forms an engagement with the sleeve element or an end stop for the sleeve element during the pressing of the sleeve element, in particular for its projection or step. Of course, it would also be conceivable that the through-opening has a plurality of recesses or steps. In particular, it would be conceivable that the recess has a groove which is extended in the circumferential direction and in which the sleeve element can form-fittingly engage with projections or other engagement portions. In contrast, the formation of a step is easy to manufacture and the sleeve element can be moved easily to the stop in the correct mounting position, preferably with a correspondingly configured step in the press-in direction.

Furthermore, it proves to be advantageous that the ilium screw is cannulated and in that the sleeve element has a through-opening aligned with the first longitudinal direction and thus with the cannulation. In this way, the ilium screw can also be supplied via a guide wire during implantation after the insertion of the sleeve element.

It is further proposed that the distal nominal diameter of the distal threaded portion of the ilium screw is at least 5.0 mm, in particular at least 6.0 mm, in particular at least 7.0 mm and is not more than 10.5 mm, in particular not more than 9.5 mm, in particular not more than 8.5 mm.

It is further proposed that the outer diameter of the thread-free portion in the region of the through-opening is at least 9.0 mm, in particular at least 10.0 mm and at most 14.5 mm, in particular at most 13.5 mm, in particular at most 12.5 mm.

It is further proposed that the proximal nominal diameter of the proximal threaded portion of the ilium screw is at least 10.0 mm, in particular at least 11 mm and at most 16.5 mm, in particular at most 15.5 mm, in particular at most 14.5 mm.

According to a further embodiment of the invention, it proves to be particularly advantageous that an outer diameter of the ilium screw decreases starting from the thread-free portion and from a position distal to the through-opening in the distal direction as far as the distal threaded portion, and tapers in particular in the distal core diameter of the distal threaded portion. As a result of this further configuration feature, the ilium screw is designed with a smaller outer diameter in a distal region which can extend in the longitudinal direction, in particular to the middle of the ilium screw. This proves to be advantageous because the bone strength of the ilium is typically lower or decreasing in the region where the ilium screw comes to lie distally.

In this case, it may prove to be advantageous that an outer diameter of the ilium screw decreases starting from the thread-free portion and from a position distal to the through-opening in the distal direction as far as the distal threaded portion and that in the region of decreasing outer diameter of the ilium screw another external thread is formed having a accordingly decreasing nominal diameter. In this way, the thread-free portion of the ilium screw, in which the through-opening is formed, can be anchored even more stably supporting the ilium by means of the distally adjacent threaded portion.

The proximal end of the ilium screw can be designed without any special restrictions. However, it can prove to be advantageous that at a proximal end portion of the ilium screw a ball head portion can be fixed, in particular screwed into an internal thread provided there, wherein the ball head portion is accommodated in a fixed manner in a further fork-shaped receiving part in a selectable orientation, wherein a rod can also be fixed on the receiving part, said rod being fixable by means of a further bone anchor with respect to a spinal column segment. This opens up the possibility that the bone anchor fixed in the ilium and sacrum can be rigidly coupled in addition to one or more spinal segments, if this proves to be advisable from a medical point of view.

It can also prove to be advantageous that a cap can be fixed to a proximal end region of the ilium screw, in particular screwed into a female thread provided there.

Furthermore, it may prove to be advantageous that the proximal end region of the ilium screw has an axial opening having an internal thread into which the ball head portion or the cap can be screwed with a respective external thread portion.

Advantageously, the proximal end portion of the ilium screw is formed with a tool attachment point, which makes it possible to quickly produce and release again a rotary coupling with a tool.

Furthermore, it proves to be advantageous that a tool for screwing the ilium screw and/or a target template can be detachably attached, by means of which a guide wire can extend through and be arranged in the sacrum in a targeted manner and in a preselected orientation with respect to the through-opening in the ilium screw.

It also proves to be advantageous that the ilium screw has a tool attachment point at a proximal end region, having a marking indicating the press-in direction or clip-in direction of the sleeve element and thus its orientation with respect to an end stop in the through-opening.

The iliosacral screw is preferably formed with a head having a tool attachment point, for example an Allen, Torx attachment point, said head being attachable to a shaft of the iliosacral screw or being formed integrally with the shaft.

Furthermore, it proves to be advantageous for the iliosacral screw to be cannulated. In this way, the iliosacral screw can be supplied via a guide wire during implantation.

Furthermore, it proves to be advantageous that the iliosacral screw is formed in the distal third portion having lateral perforations and thus a commercially available bone cement can be applied by the screw. As a result, additional fixation of the iliosacral screw to the sacral vertebral body can be achieved.

When screwed in, the iliosacral screw can then abut with its head against the outside of the ilium. According to a further inventive concept, it is proposed, on the other hand, that the iliosacral screw has an abutment disc for abutment with an ilium surface, which is radially cut and designed such that it can be clipped onto a constricted region in the region of a proximal end or head of the iliosacral screw and is tiltable relative to the second longitudinal direction while still being fixed, so that said abutment disc can abut to the ilium surface at an angle to the second longitudinal direction when screwing the iliosacral screw. In this way, the iliosacral screw can abut flat against its outer surface of the ilium, even if this outer side is not orthogonal to the longitudinal direction of the iliosacral screw. This proves to be particularly advantageous because a further stabilization of the screwed iliosacral screw can be achieved.

In a further development of this idea, it is proposed that the abutment disc and the proximal end or the head of the iliosacral screw have complementarily formed dome-shaped bearing surfaces.

Furthermore, it may prove to be advantageous for the abutment disc and the proximal end or head of the iliosacral screw have mutually locking means in the circumferential direction. Also advantageous is a possible large contact surface between the abutment disk and the end or head of the screw.

To further stabilize the position, it proves to be advantageous that the abutment disc has anchorage means on its side facing the ilium surface in the form of projecting serrations or pins which are able to penetrate the ilium surface when the iliosacral screw is tightened.

According to a further idea of particular practical importance, it proves to be advantageous for the abutment disk to have a radially outwardly widening radial opening delimited by flanks. With a corresponding design of the radial opening with respect to the outer diameter of the iliosacral screw, the abutment plate can then be clipped transversely to the second longitudinal direction onto the shaft and in particular onto the constricted region of the iliosacral screw by slight elastic widening. It proves to be advantageous if the flanks are rounded and/or merge in a rounded manner into an outer circumference of the abutment disk, which facilitates the clipping.

The abutment disc preferably has a maximum thickness of 3.0-6.0 mm, wherein the thickness can decrease in the radial direction to the outside.

Furthermore, it proves to be particularly advantageous if the iliosacral screw has a double-threaded thread and in the proximal threaded portion a four-turn thread which is designed to cut into the sleeve element over the full extent of the sleeve element in the first longitudinal direction.

Further protection is claimed for a general assembly comprising a bone anchor according to the invention and a polyaxial pedicle screw with a ball head portion and a fork-shaped receiving part for the ball head portion, wherein the ball head portion can be screwed with a distal threaded portion into an axial opening in a proximal end portion of the ilium screw. As stated above, this also allows the bone anchor for iliosacral osteosynthesis to be rigidly connected to one or more adjacent vertebral bodies.

Furthermore, protection is claimed for a general assembly comprising a bone anchor according to the invention and a tool for screwing in the ilium screw and a target template, wherein the tool can be fixed to a proximal end portion of the ilium screw and the target template can be fixed to the tool, and wherein the ilium screw, the tool and the target template are always fixed to each other such that a target direction of the target template always passes through the through hole of the ilium screw.

It proves to be advantageous that the target template has a target device for a wire or pin that are displaceable therein, and that the target device is adjustable with respect to an arcuate guide strut so that the straight wire or pin describes a pivot plane, wherein the angle of the straight wire or pin changes to the first longitudinal direction of the ilium screw. As a result, a specific angle or orientation between the ilium screw and the iliosacral screw can be predefined using the target template. After screwing in the ilium screw, the target template is positioned on the tool for this purpose; it can then be adjusted by means of the target device, the desired orientation and the wire or pin are guided in this desired orientation through the ilium and through the through-opening of the ilium screw into the sacrum. The wire or pin can continue to serve as a guide when screwing the iliosacral screw.

Further protection is claimed for a method having the features of claims 35 and 36.

BRIEF DESCRIPTION OF THE DRAWINGS

Further features, details and advantages of the invention can be found in the enclosed claims, in the drawings and in the following description of a preferred embodiment of the bone anchor according to the invention. In the drawings:

DETAILED DESCRIPTION

Figure 1:
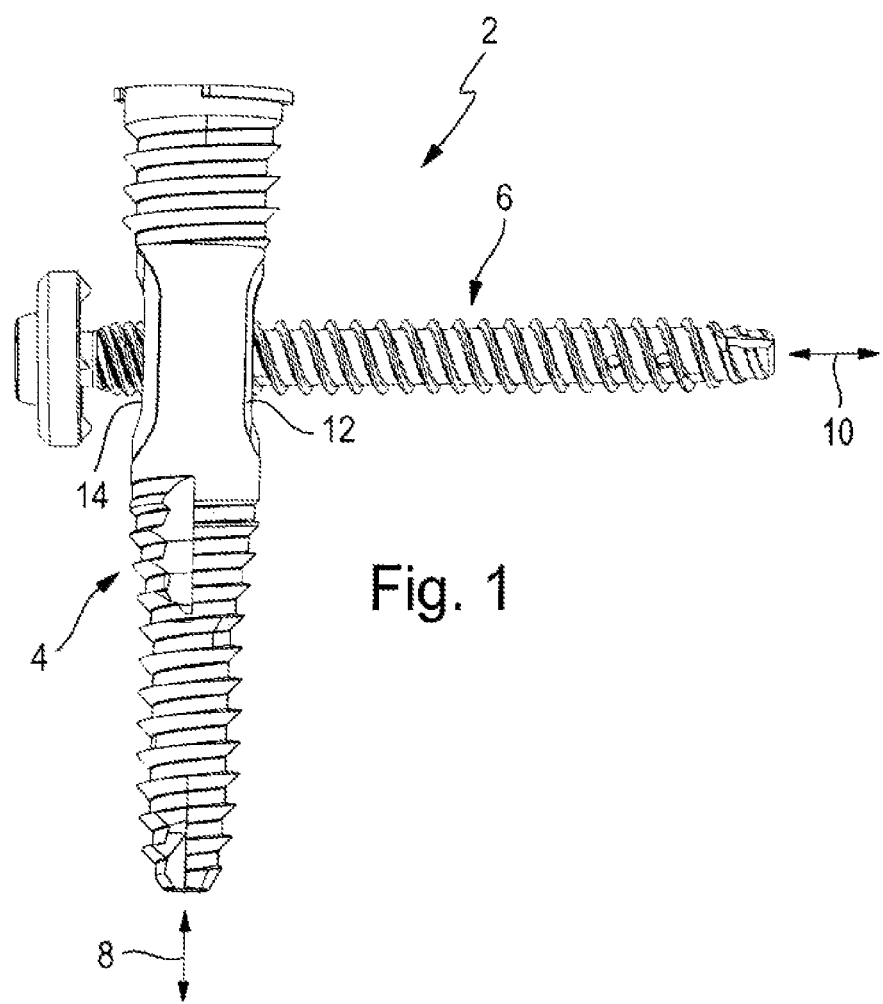
FIG. 1 shows a side view of an inventive bone anchor for triangular iliosacral osteosynthesis, having an ilium screw and an iliosacral screw.
Figure 2A:
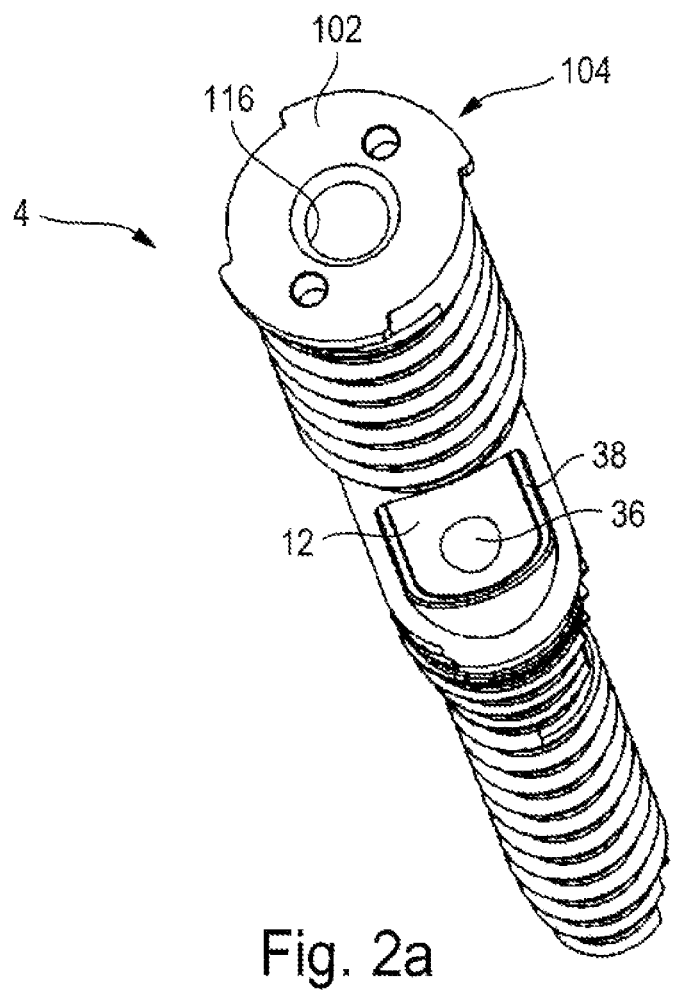
FIGS. 2 *a*)-*d*) show different views of the ilium screw according to FIG. 1 without sleeve element.
Figure 2D:
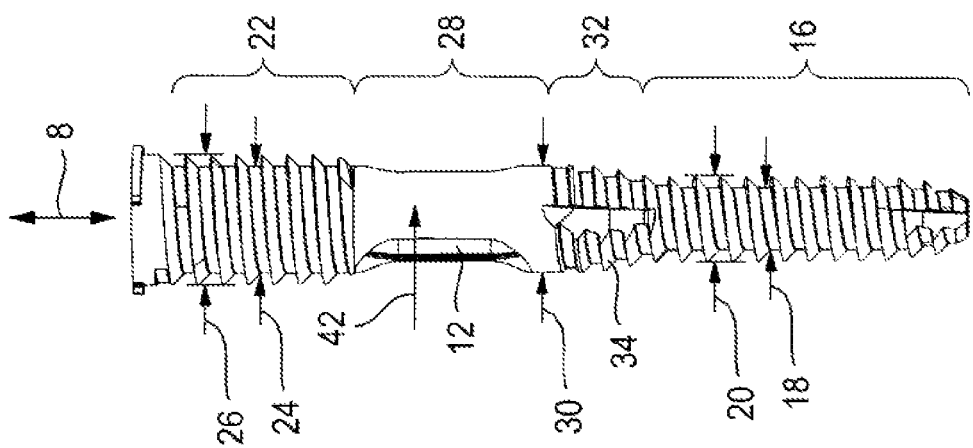
Figure 2C:
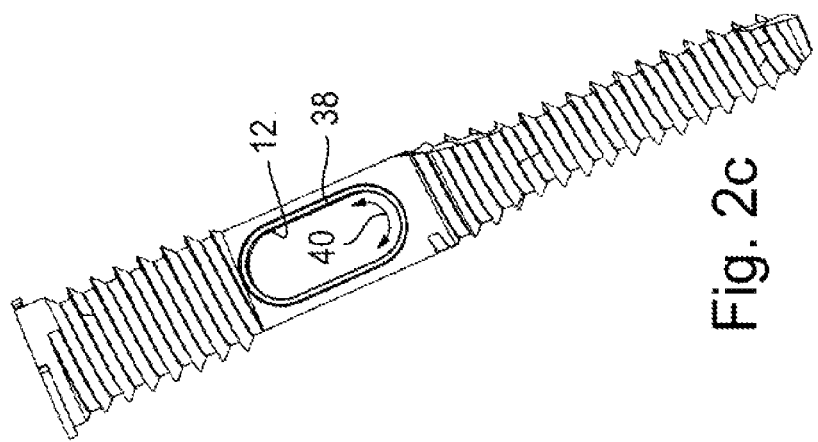
Figure 2B:
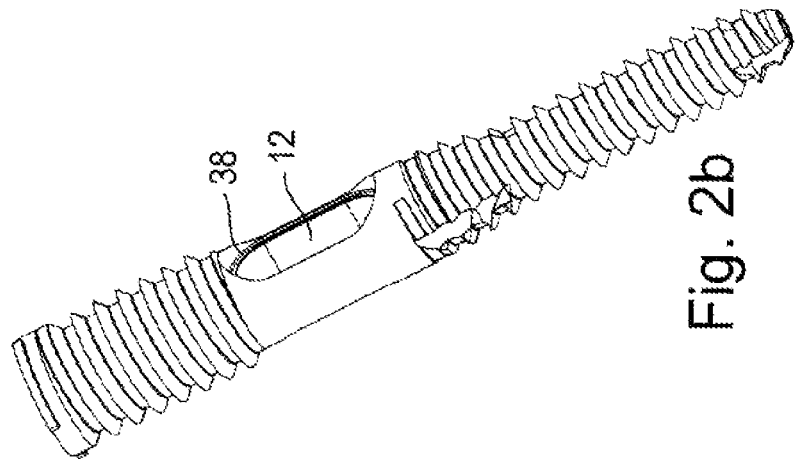

FIG. 1 shows a bone anchor for triangular iliosacral osteosynthesis, indicated overall by the reference numeral 2, having an ilium screw 4 and an iliosacral screw 6. The ilium screw 4 forms a first longitudinal direction 8, and the iliosacral screw 6 forms a second longitudinal direction 10, which are shown orthogonally only as an example. The ilium screw 4 is formed with a preferably slot-shaped through-opening 12 through which the iliosacral screw 6 can extend. In the intended application of the triangular iliosacral osteosynthesis, first the ilium screw 4 is screwed into the ilium, and thereafter the iliosacral screw 6 is screwed through the through-opening 12 into the sacrum. For this purpose, the ilium screw 4 has—as will be described in detail—a sleeve element 14 in the through-opening 12 made of a polymer material, said sleeve element being inserted into the through-opening 12. In the screwed-in state of the iliosacral screw 6, their threads intersect the sleeve element 14 and thus give the iliosacral screw 6 a better hold relatively to the ilium screw 4.

Figure 3A:
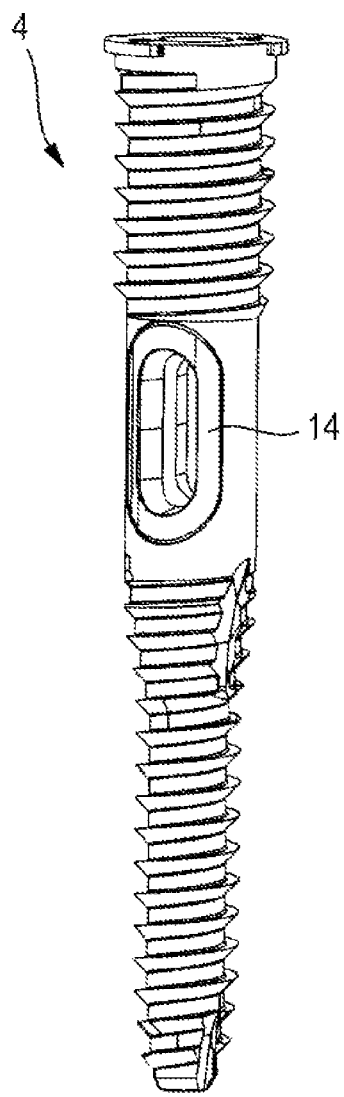
FIGS. 3 *a*)-*b*) show different views of the ilium screw of FIG. 2, but having an inserted sleeve element.
Figure 3B:
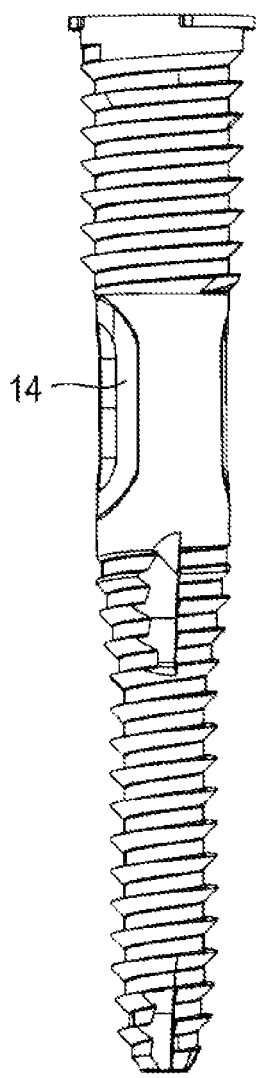
Figure 4A:
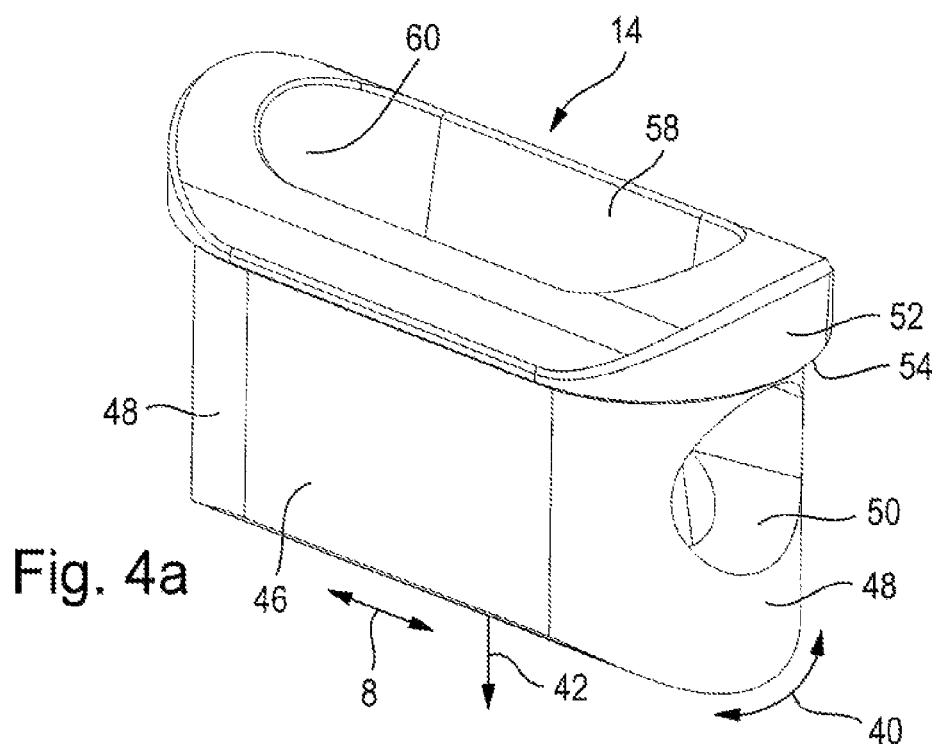
FIGS. 4 *a*)-*c*) show different views of the sleeve element.
Figure 4B:
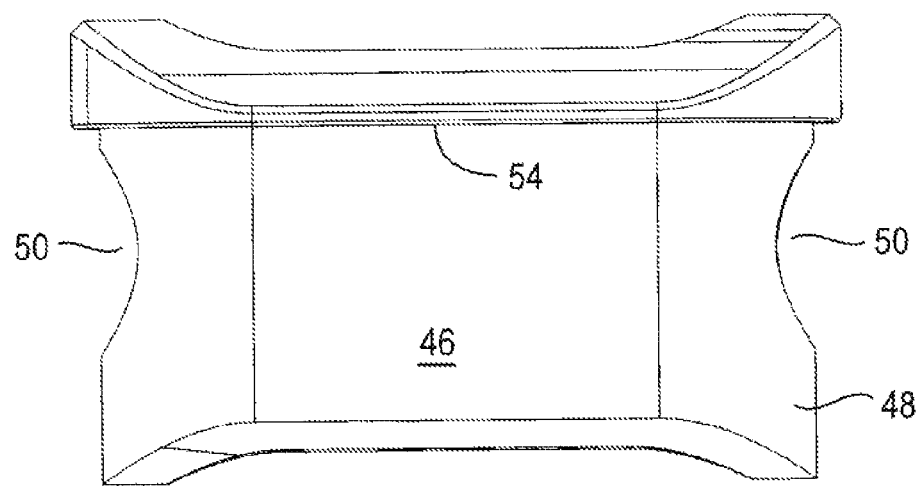

The ilium screw 4 is shown without this sleeve element 14 in FIGS. 2 *a*) to *d*) and with inserted sleeve element in FIGS. 3 *a*), *b*). The sleeve element 14 is also shown in FIGS. 4 *a*)-*c*).

The ilium screw 4 has a distal threaded portion 16 having a distal core diameter 18 and a nominal distal diameter 20, and a proximal threaded portion 22 having a proximal core diameter 24 and a proximal nominal diameter 26 of the thread. In between, a thread-free portion 28 is provided, in which the preferably slot-shaped through-opening 12 is formed transversely and orthogonal to the first longitudinal direction 8. The proximal nominal diameter 26 of the proximal threaded portion 22 is greater than an outer diameter of the thread-free portion 28, and the outer diameter 30 of the thread-free portion 28 is greater than the nominal distal diameter 20. Starting from the thread-free portion 28, namely from a position distal to the through-opening 12, the outer diameter of the ilium screw 4 decreases in the distal direction as far as the distal threaded portion 16. In this region 32 of decreasing outer diameter, a thread 34 is also provided, which then merges into the thread of the distal threaded portion 32. An opening can also be seen from FIG. 2 *a*), said opening extending as a longitudinal central opening 36 through the entire ilium screw 4 and forming a cannulation of the ilium screw.

The through-opening 12 of the ilium screw 4 is formed having a step 38. In the case illustrated by way of example, this step 38 forms a step or contact surface for the sleeve element 14 that extends continuously in a circumferential direction 40 of the through-opening 12. Instead of the step 38, one or more webs or recesses, in particular a groove extending in the circumferential direction 40, could be provided, with which the sleeve element 14 can interact in a supporting manner, thereby forming a form-fit engagement in the press-in direction 42 or in the opposite direction. The press-in direction 42 is orthogonal to the first longitudinal direction 8.

The sleeve element 14 (see FIGS. 4 *a*)-*c*)) is likewise of elongated shape and comprises a wall 46 which is closed in the circumferential direction 40 and has two parallel wall portions 48 which extend in the first longitudinal direction 8 and which have two oval or semicircular wall portions 48 connecting these wall portions 48 in the circumferential direction 40. In the wall portions 48, aligned openings 50 are formed with the longitudinal central opening 36 of the ilium screw.

The sleeve element 14 has, in the case illustrated by way of example, a projection 52 projecting transversely to its press-in direction 42, by means of which the sleeve element 14 forms a form-fit engagement with the ilium screw 4 when it is inserted into the through-opening 12 in the press-in direction 42. In the example illustrated, the projection 52 forms a step 54 on the sleeve element 14, said step being formed continuously in the circumferential direction 40 and forming a continuous flange 56 in the sleeve element 14. With this flange 56, the sleeve element 14 abuts against the step 38 in the pressed-in state, said step being formed in the insertion opening 12 of the ilium screw 4. As a result, a form-fitting engagement in the press-in direction 42 is formed, that is, when further forces act in the press-in direction 42, such that the sleeve element 14 cannot be pushed in the press-in direction 42 through the through-opening 12, but is held in a form-fitting manner by the steps 38, 54 abutting against each other. Alternatively, a groove/spring system would be conceivable or another design of a form-fit engagement of the sleeve element 14 and the ilium screw 4 would be conceivable and advantageous, said form-fit engagement acting in the press-in direction 42 and in the opposite direction. If the sleeve element 14 was form-fittingly held in both directions, no preferential orientation for screwing the iliosacral screw 6 would exist.

Overall, the projection 52 is formed on the sleeve element 14 so that it merges flush in the inserted state of the sleeve element 14 and continuously into the outer periphery of the thread-free portion 28. The projection 52 effectively completes the outer circumference of the thread-free portion 28. Furthermore, the sleeve element 14 in turn defines a slot-shaped through-opening with mutually parallel inner sides 58 of the wall portions 46 and with curved inner sides 60 of the wall portions 48.

Figure 5B:
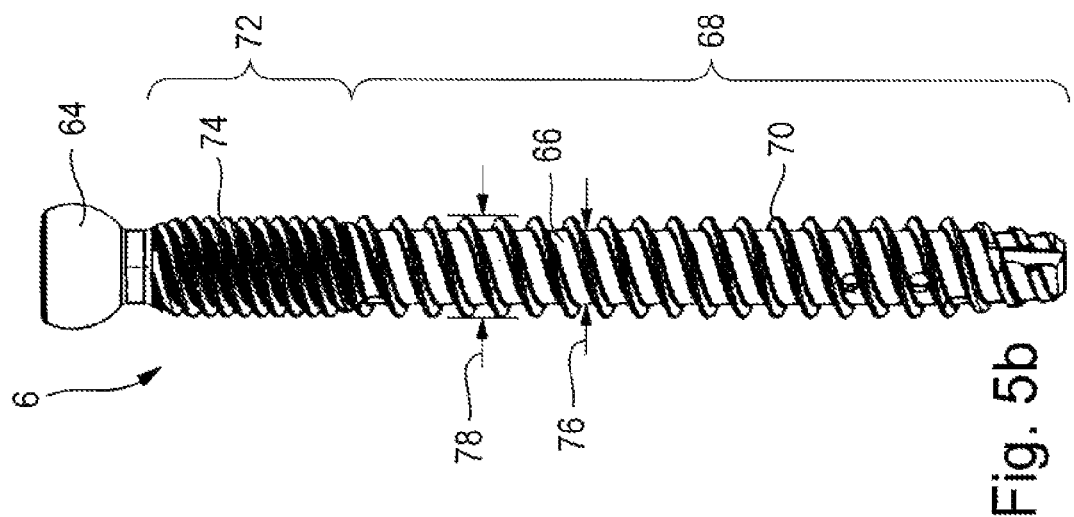
FIGS. 5 *a*), *b*) show different views of the iliosacral screw according to FIG. 1.
Figure 5A:
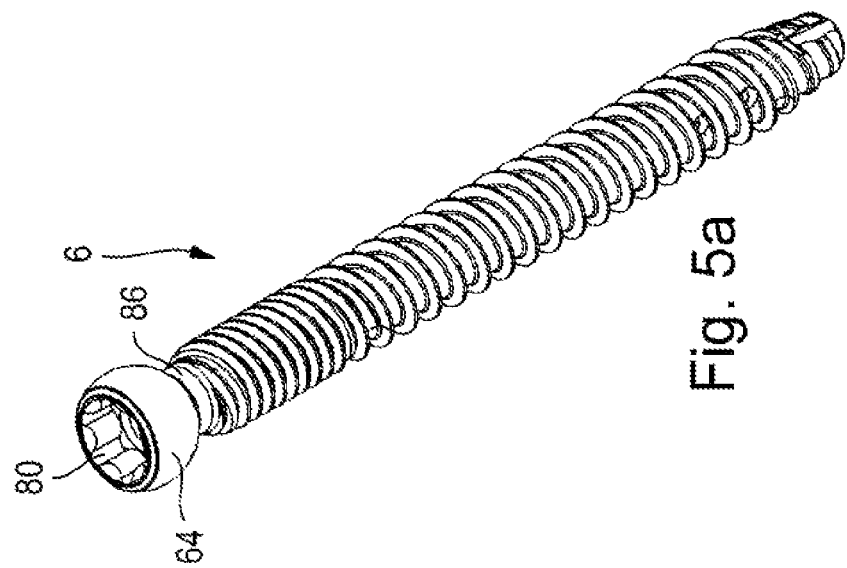

FIGS. 5 *a*), *b*) show views of the iliosacral screw 6. It comprises a head 64 and a screw shaft 66. The screw shaft 66 preferably has a distal threaded portion 68 with an exemplary double-threaded external thread 70 and a proximal threaded portion 72 with an exemplary four-start thread 74. The threads 70, 74 have, for example, the same core and nominal diameter. When screwing the iliosacral screw 6 through the through-opening 12 of the ilium screw 4, the threads 70, 74 cut into the wall portion 46 and possibly 48 of the sleeve element 14. When screwing, a tensile force is exerted on the sleeve element 14 in the second longitudinal direction 10. Due to the form-fit engagement of the sleeve element 14 with the ilium screw 4, however, there is no danger of the sleeve element 14 being pulled out of or being pulled through the through-opening 12 of the ilium screw 4 when the iliosacral screw 6 is screwed in. Rather, the material of the sleeve element 14 is displaced by the cutting of the thread 70, 74 of the iliosacral screw 6 and is even more compressed in the through-opening 12 of the ilium screw 4. The iliosacral screw 6 has, in the case illustrated by way of example, an Allen-shaped or Torx-shaped tool attachment point 80 on the head 64.

The iliosacral screw is cannulated. In this way, the iliosacral screw can be supplied via a guide wire during implantation.

The iliosacral screw is formed in the distal third portion having lateral perforations. Thus, commercially available bone cement can be applied by the screw. As a result, additional fixation of the iliosacral screw in the sacral vertebral body can be achieved.

Figure 6A:
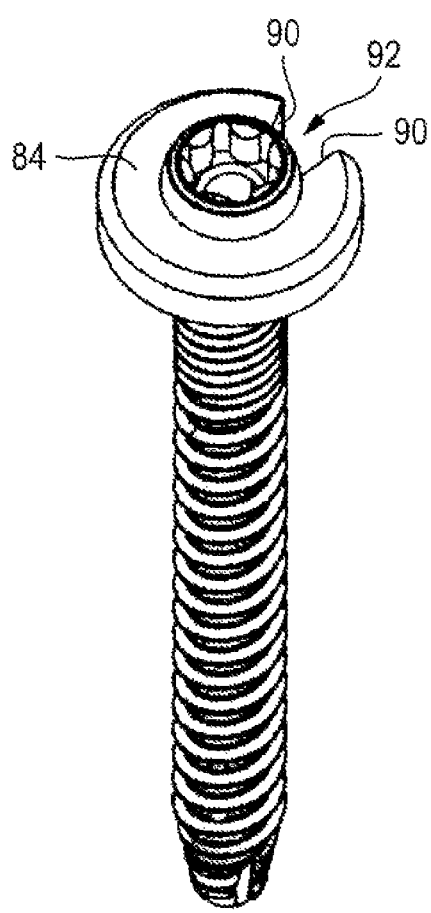
FIGS. 6 *a*), *b*) show different views of the iliosacral screw according to FIG. 5, but with an abutment disc.
Figure 6B:
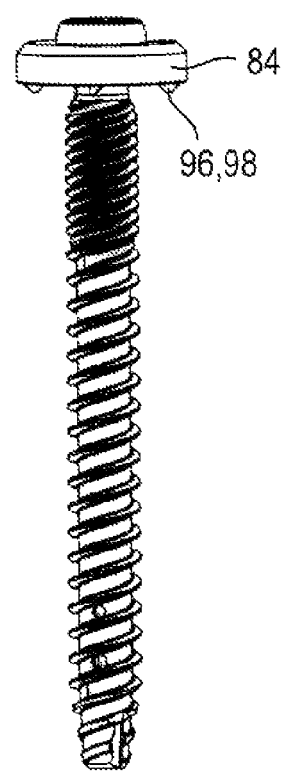
Figure 7A:
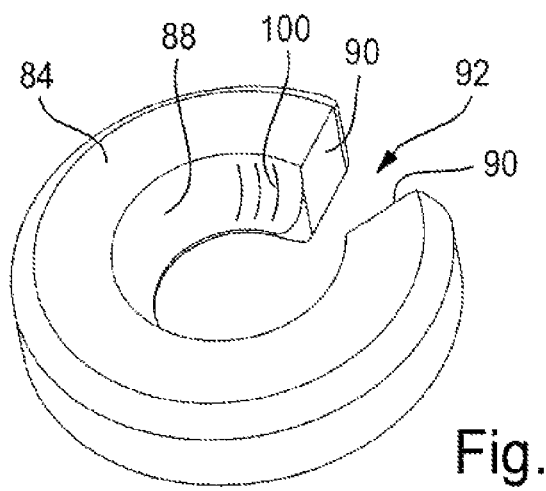
FIGS. 7 *a*)-*c*) show views of the abutment disk according to FIG. 6.
Figure 7B:
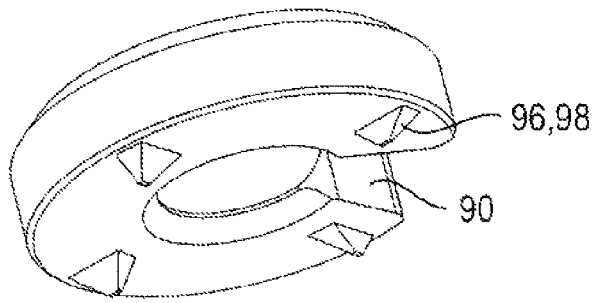
Figure 7C:
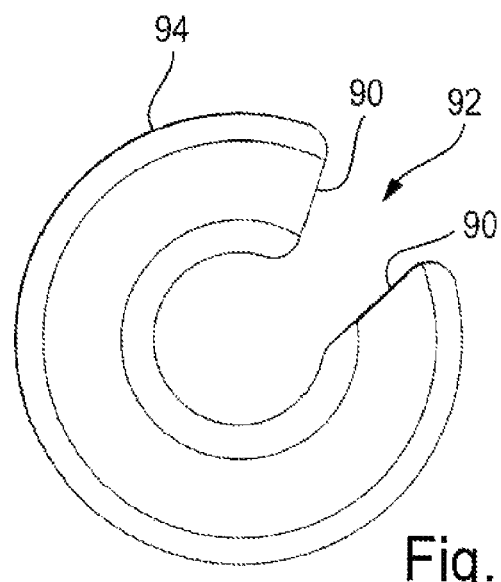
Figure 8A:
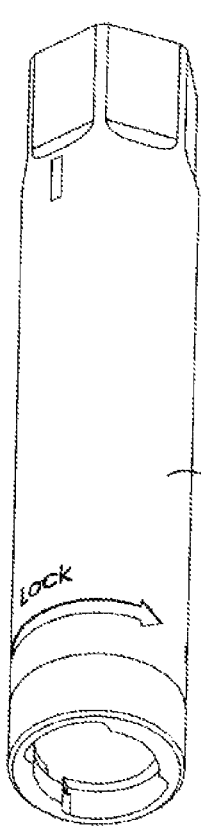
FIGS. 8 *a*)-*c*) show views of a screwdriving tool having a coupling sleeve and a turning handle.
Figure 8B:
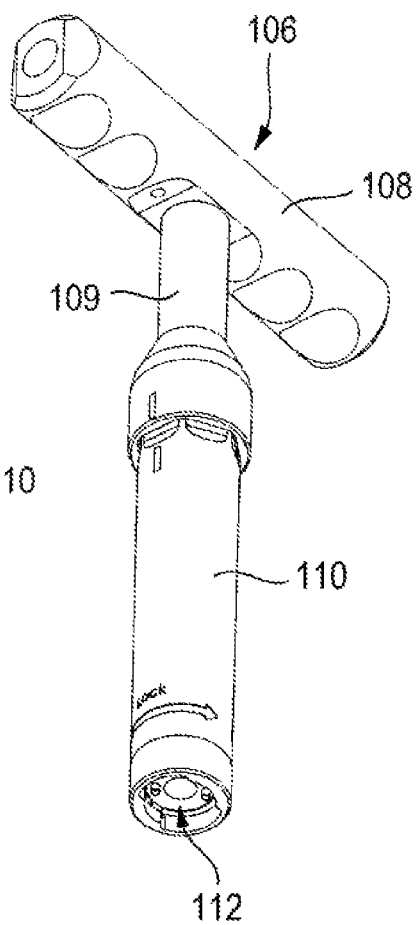
Figure 8C:
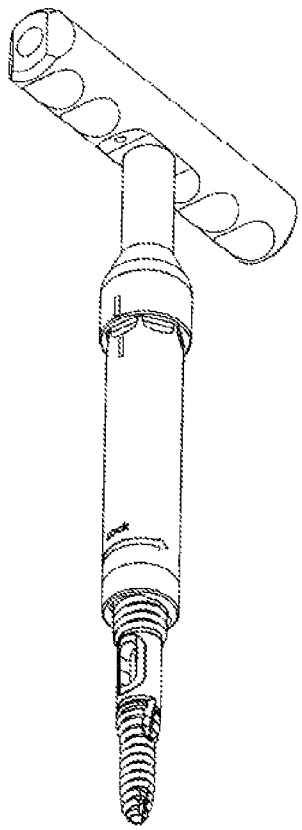

FIGS. 6 *a*), *b*) further show a contact disk 84, which is radially cut and designed such that it can be pushed, in particular can be clipped, onto a constricted region 86 of the iliosacral screw 6 between the head 64 and the proximal threaded portion 72. The abutment disk 84 is tiltable in this state to the second longitudinal direction 10, but preferably held captive on the iliosacral screw 6. Between the abutment disc 84 and the iliosacral screw 6, complementary dome-shaped bearing surfaces 88 are formed. Thus, the abutment disc 84 can also be inclined to the second longitudinal direction 10 against an outer surface of the ilium surface when the iliosacral screw 6 is tightened. The contact disk 84 preferably has a radial opening 92 that widens radially outward and is delimited by flanks 90. The flanks 90 are preferably rounded or at least merge in a rounded manner into an outer circumference 94 of the abutment disk 84. The abutment disc 84 comprises anchoring means 96 on its side facing the ilium, said anchoring means being in the form of protruding serrations or pins 98, with which the abutment disc 84 can penetrate into the bone surface of the ilium, whereby the anchoring is further improved. In the region of the bearing surfaces 88 between the bearing plate 84, only schematically indicated locking means 100 may be provided.

At the proximal end portion 102 of the ilium screw 4, a tool attachment point 104 is also formed on which a rotary tool 106 is rotatably attached with a handle 108, a rotary spindle 109 and a sleeve 110. The rotary spindle 109 includes at its distal end complementary to the proximal end portion 102 formed rotary coupling means or engagement means 112. The handle 108, the rotary spindle 109 and the sleeve 110 are rotatably coupled to the ilium screw 4, so that the ilium screw 4 can be screwed into the ilium. The rotary tool 116 and its components are designed so that they can be fixed to the ilium screw only in a maximum of two rotational positions that are different from each other by 180°. Rotary tool 116 effectively the position of the through hole 12 of the ilium screw.

Figure 9C:
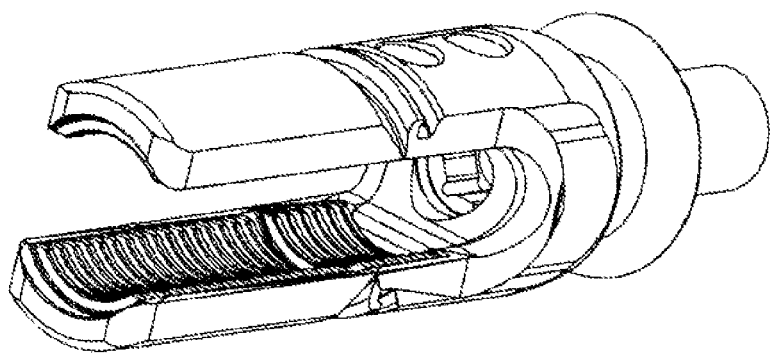
FIGS. 9 *a*)-*c*) show a spherical head portion mounted in a pedicle screw.
Figure 9B:
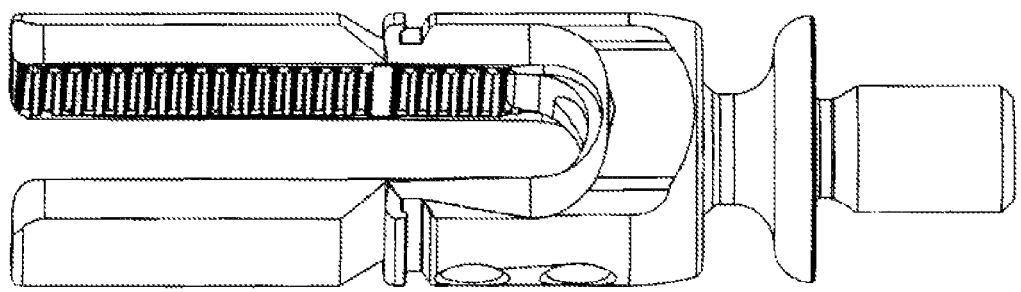
Figure 9A:
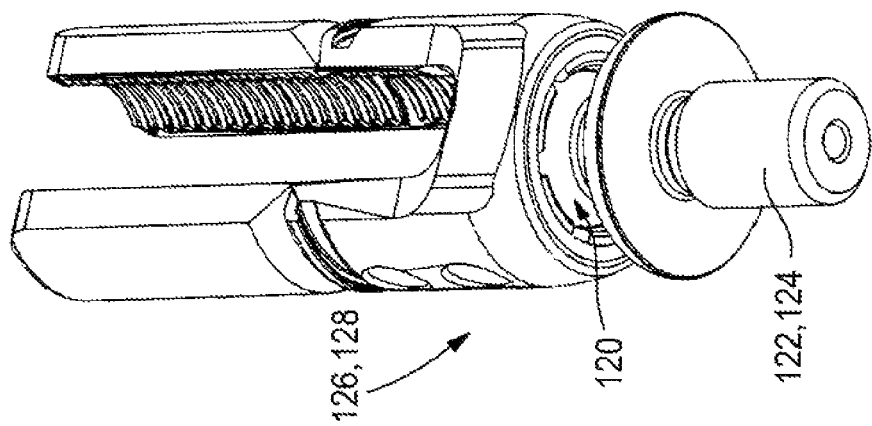

FIGS. 9a-c) show a ball head portion 120 with a shaft portion 122 with a distal threaded portion 124, which in turn can be screwed into the threaded opening 116 at the proximal end portion 102 of the ilium screw 4. The ball head portion 120 is pivotally received in a fork-shaped receiving part 126 of a polyaxial pedicle screw 128. In the fork-shaped receiving part 126, a rod can be fixed in a conventional manner, by means of which the pedicle screw can be connected to adjacent pedicle screws.

Figure 10A:
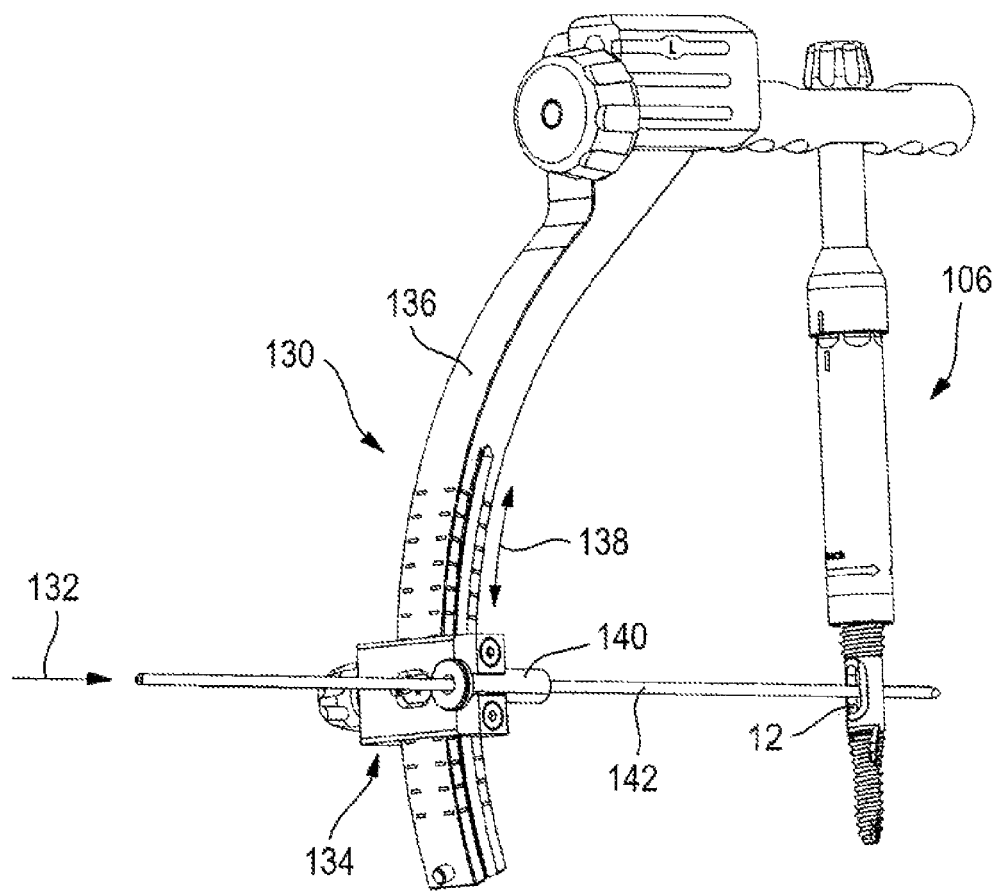
FIGS. 10 *a*), *b*) show views of a target template cooperating with an ilium screw.
Figure 10B:
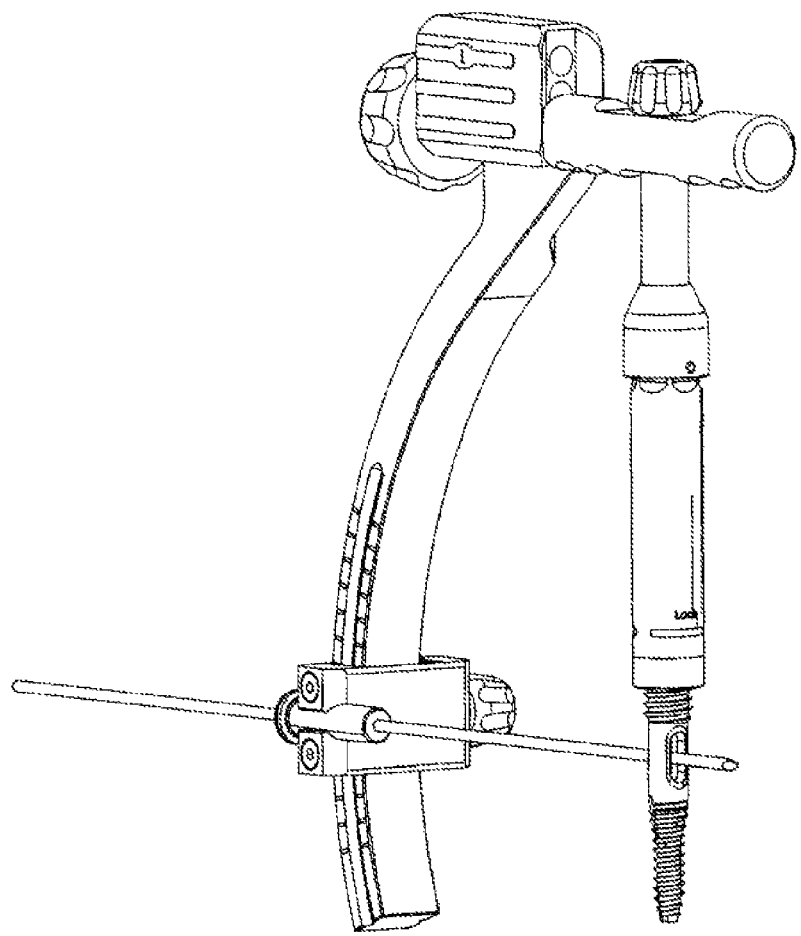

Finally, FIGS. 10a, b) show a target template 130 which can be fastened to the rotary tool 106 such that a target direction 132 of the target template 130 always extends through the through-opening 12 in the ilium screw 4. For this purpose, the rotary tool 106 can be attached to the ilium screw 4 only in one or at most two specific orientations relative to the through-opening 12. By virtue of the fact that the target template 130 can then in turn be fixed to the rotary tool 106 in a predetermined orientation, this alignment can be achieved automatically. The target template 130 comprises a target device 134 which is adjustable in the direction of the double arrow 138 with respect to an arcuate guide strut 136. The target device 134 comprises a receptacle 140, in which a wire or pin 142 can be guided in a longitudinally displaceable manner in the longitudinal direction 132. This wire or pin 142 predetermines the second longitudinal direction 10 for the iliosacral screw 6 with suitable alignment of the target template 130.

Furthermore, FIG. 2 a) shows a threaded opening 116, which extends in the first longitudinal direction, starting from the proximal end region 102. In this threaded opening a cap or a ball head portion can be screwed.

The invention claimed is:

1. Bone anchor for triangular iliosacral osteosynthesis, comprising an ilium screw having a first longitudinal direction and an iliosacral screw having a second longitudinal direction, wherein the ilium screw, in a thread-free portion, has an elongated through-opening formed transversely to the first longitudinal direction, and the iliosacral screw has such a smaller outer diameter in relation to the ilium screw that the iliosacral screw can be guided through said through-opening and can be screwed proceeding from the ilium into the sacrum, through the ilium screw, wherein the ilium screw has a distal threaded portion having a distal core diameter and a distal nominal diameter of the thread and a proximal threaded portion having a proximal core diameter and a proximal nominal diameter of the thread, and wherein the thread-free portion is arranged between the distal and the proximal threaded portion, wherein the proximal nominal diameter is greater than an outer diameter of the thread-free portion and the outer diameter of the thread-free portion is greater than the distal nominal diameter, and wherein a sleeve element having an inner diameter and a shape complementary to a shape of the elongated through-opening and made of a polymer material is inserted into the through-opening and is then held in the through-opening frictionally and additionally in a form-fitting manner relative to at least one direction, wherein the inner dimension of the sleeve element orthogonally to the first longitudinal direction is smaller than a nominal diameter of a thread of the iliosacral screw.

2. Bone anchor according to claim 1, characterized in that the sleeve element consists of a polymer material that is dimensionally stable, but slightly flexibly deformable, in particular elastically deformable, such that it can be slightly oversized with respect to the through-opening and can then be pressed with slight deformation into the through-opening.

3. Bone anchor according to claim 2, characterized in that the sleeve element is made of polyethylene, PEEK, PEAK, PEKK, PPSU or PPS.

4. Bone anchor according to claim 1, characterized in that an inner dimension of the through-opening orthogonally to the first longitudinal direction is at least 6.0 mm and at most 11.5 mm.

5. Bone anchor according to claim 1, characterized in that an inner dimension of the sleeve element that is orthogonal to the first longitudinal direction is smaller than a core diameter of a thread of the iliosacral screw.

6. Bone anchor according to claim 1, characterized in that a nominal diameter of a thread of the iliosacral screw is at least 6 mm and at most 9.5 mm.

7. Bone anchor according to claim 1, characterized in that the sleeve element has a wall thickness of at least 1.0 mm and at most 3.0 mm.

8. Bone anchor according to claim 1, characterized in that the sleeve element has at least one projection projecting transversely to its press-in direction, by means of which a form-fit engagement of the sleeve element with the ilium screw is achieved.

9. Bone anchor according to claim 8, characterized in that the projection forms a step on the sleeve element.

10. Bone anchor according to claim 8, characterized in that the projection or the step is extended in a circumferential direction of the sleeve element.

11. Bone anchor according to claim 8, characterized in that the projection or the step forms a broken or continuous flange on the sleeve element in the circumferential direction.

12. Bone anchor according to claim 8, characterized in that the through-opening is formed with a recess or step which forms an engagement with the sleeve element or an end stop for the sleeve element during the pressing of the sleeve element for its projection or step.

13. Bone anchor according to claim 1, characterized in that the ilium screw is cannulated and in that the sleeve element has a through-opening aligned with the first longitudinal direction and thus with the cannulation.

14. Bone anchor according to claim 1, characterized in that the distal nominal diameter of the distal threaded portion of the ilium screw is at least 5.0 mm and is not more than 10.5 mm.

15. Bone anchor according to claim 1, characterized in that the outer diameter of the thread-free portion in the region of the through-opening is at least 9.0 mm and at most 14.5 mm.

16. Bone anchor according to claim 1, characterized in that the proximal nominal diameter of the proximal threaded portion of the ilium screw is at least 10.0 mm and is not more than 16.5 mm.

17. Bone anchor according to claim 1, characterized in that an outer diameter of the ilium screw decreases starting from the thread-free portion and from a position distal to the through-opening in the distal direction as far as the distal threaded portion, and tapers in particular in the distal core diameter of the distal threaded portion.

18. Bone anchor according to claim 1, characterized in that an outer diameter of the ilium screw decreases starting from the thread-free portion and from a position distal to the through-opening in the distal direction as far as the distal threaded portion, and that in the region of the decreasing outside diameter of the ilium screw a further outside thread having a decreasing nominal diameter is formed.

19. Bone anchor according to claim 1, characterized in that at a proximal end portion of the ilium screw a ball head portion can be fixed, wherein the ball head portion is accommodated in a fixed manner in a further fork-shaped receiving part in a selectable orientation, wherein a rod can also be fixed on the receiving part, said rod being fixable by means of a further bone anchor with respect to a spinal column segment.

20. Bone anchor according to claim 19, characterized in that at a proximal end portion of the ilium screw a cap can be fixed.

21. Bone anchor according to claim 20, characterized in that the proximal end region of the ilium screw has an axial opening having an internal thread into which the ball head portion or the cap can be screwed with a respective external thread portion.

22. Bone anchor according to claim 1, characterized in that at a proximal end portion of the ilium screw a tool for screwing the ilium screw and/or a target template can be detachably attached, by means of which a guide wire can extend through and be arranged in the sacrum in a targeted manner and in a preselected orientation with respect to the through-opening in the ilium screw.

23. Bone anchor according to claim 1, characterized in that the ilium screw has a tool attachment point at a proximal end region, having a marking indicating the press-in direction or clip-in direction of the sleeve element and thus its orientation with respect to an end stop in the through-opening.

24. Bone anchor according to claim 1, characterized in that the iliosacral screw has an abutment disc for abutment with an ilium surface, which is radially cut and designed such that it can be clipped onto a constricted region in the region of a proximal end or head of the iliosacral screw and is tiltable relative to the second longitudinal direction while still being fixed, so that said abutment disc can abut to the ilium surface at an angle to the second longitudinal direction when screwing the iliosacral screw.

25. Bone anchor according to claim 24, characterized in that the abutment disc and the proximal end or head of the iliosacral screw have complementarily formed dome-shaped bearing surfaces.

26. Bone anchor according to claim 24, characterized in that the abutment disc and the proximal end or head of the iliosacral screw have mutually locking means in a circumferential direction.

27. Bone anchor according to claim 24, characterized in that the abutment disc has anchorage means on its side facing the ilium surface in the form of projecting serrations or pins which are able to penetrate the ilium surface when the iliosacral screw is tightened.

28. Bone anchor according to claim 24, characterized in that the abutment disc has a radial opening that widens radially outward and is delimited by flanks.

29. Bone anchor according to claim 28, characterized in that the flanks are rounded and/or merge in a rounded manner into an outer circumference of the abutment disk.

30. Bone anchor according to claim 24, characterized in that the abutment disc has a maximum thickness of 3.0-6.0 mm, wherein the thickness can decrease in the radial direction to the outside.

31. Bone anchor according to claim 1, characterized in that the iliosacral screw has a double-threaded thread and in the proximal threaded portion a four-turn thread which is designed to cut into the sleeve element over the full extent of the sleeve element in the first longitudinal direction.

32. Assembly comprising a bone anchor for triangular iliosacral osteosynthesis, comprising an ilium screw having a first longitudinal direction and an iliosacral screw having a second longitudinal direction, wherein the ilium screw, in a thread-free portion, has an elongated through-opening formed transversely to the first longitudinal direction, and the iliosacral screw has such a smaller outer diameter in relation to the ilium screw that the iliosacral screw can be guided through said through-opening and can be screwed proceeding from the ilium into the sacrum, through the ilium screw, wherein the ilium screw has a distal threaded portion having a distal core diameter and a distal nominal diameter of the thread and a proximal threaded portion having a proximal core diameter and a proximal nominal diameter of the thread, and wherein the thread-free portion is arranged between the distal and the proximal threaded portion, wherein the proximal nominal diameter is greater than an outer diameter of the thread-free portion and the outer diameter of the thread-free portion is greater than the distal nominal diameter, and wherein a sleeve element having an inner diameter and a shape complementary to a shape of the elongated through-opening and made of a polymer material is inserted into the through-opening and is then held in the through-opening frictionally and additionally in a form fitting manner relative to at least one direction, wherein the inner dimension of the sleeve element orthogonally to the first longitudinal direction is smaller than a nominal diameter of a thread of the iliosacral screw, and a polyaxial pedicle screw having a ball head portion and a fork-shaped receiving part for the ball head portion, wherein the ball head portion can be screwed with a distal threaded portion into an axial opening in a proximal end portion of the ilium screw.

33. Assembly comprising a bone anchor for triangular iliosacral osteosynthesis, comprising an ilium screw having a first longitudinal direction and an iliosacral screw having a second longitudinal direction, wherein the ilium screw, in a thread-free portion, has an elongated through-opening formed transversely to the first longitudinal direction, and the iliosacral screw has such a smaller outer diameter in relation to the ilium screw that the iliosacral screw can be guided through said through-opening and can be screwed proceeding from the ilium into the sacrum, through the ilium screw, wherein the ilium screw has a distal threaded portion having a distal core diameter and a distal nominal diameter of the thread and a proximal threaded portion having a proximal core diameter and a proximal nominal diameter of the thread, and wherein the thread-free portion is arranged between the distal and the proximal threaded portion, wherein the proximal nominal diameter is greater than an outer diameter of the thread-free portion and the outer diameter of the thread-free portion is greater than the distal nominal diameter, and wherein a sleeve element having an inner diameter and a shape complementary to a shape of the elongated through-opening and made of a polymer material is inserted into the through-opening and is then held in the through-opening frictionally and additionally in a form fitting manner relative to at least one direction, wherein the inner dimension of the sleeve element orthogonally to the first longitudinal direction is smaller than a nominal diameter of a thread of the iliosacral screw, and a tool for screwing in the ilium screw and a target template, wherein the tool can be fixed to a proximal end portion of the ilium screw and the target template can be fixed to the tool, and wherein the ilium screw, the tool and the target template are always fixed to each other such that a target direction of the target template always passes through the through hole of the ilium screw.

34. Assembly according to claim 33, characterized in that the target template has a target device for a wire or pin that are displaceable therein, and that the target device is adjustable with respect to an arcuate guide strut so that the straight wire or pin describes a pivot plane, wherein the angle of the straight wire or pin changes to the first longitudinal direction of the ilium screw.

35. Method for performing a triangular iliosacral osteosynthesis using a bone anchor having an ilium screw having a first longitudinal direction and an iliosacral screw having a second longitudinal direction, wherein the ilium screw, in a thread-free portion, has an elongated through-opening formed transversely to the first longitudinal direction, and the iliosacral screw has such a smaller outer diameter in relation to the ilium screw that the iliosacral screw can be guided through said through-opening and can be screwed proceeding from the ilium into the sacrum, through the ilium screw, wherein the ilium screw has a distal threaded portion having a distal core diameter and a distal nominal diameter of the thread and a proximal threaded portion having a proximal core diameter and a proximal nominal diameter of the thread, and wherein the thread-free portion is arranged between the distal and the proximal threaded portion, wherein the proximal nominal diameter is greater than an outer diameter of the thread-free portion and the outer diameter of the thread-free portion is greater than the distal nominal diameter, and wherein a sleeve element having an inner diameter and a shape complementary to a shape of the elongated through-opening and made of a polymer material is inserted into the through-opening and is then held in the through-opening frictionally and additionally in a form-fitting manner relative to at least one direction, wherein the inner dimension of the sleeve element orthogonally to the first longitudinal direction is smaller than a nominal diameter of a thread of the iliosacral screw, characterized in that a first opening is formed in the ilium of a patient to be treated for screwing in the ilium screw,
 that the ilium screw is screwed in this opening such that the through hole thereof is positioned in such a way that the iliosacral screw can be screwed in a position and orientation intended by the surgeon,
 that a second opening is formed which extends, at an angle transverse to the first opening, through the ilium and through the passageway of the ilium screw into the sacrum of the patient to be treated,
 that the iliosacral screw is screwed into the second opening and thereby cuts into the sleeve element, which is arranged in the through hole of the ilium screw, wherein said iliosacral screw is arranged thereby in an inclination to the first longitudinal direction of the ilium screw and to the through hole of the ilium screw as intended by the surgeon, wherein this inclination is such that it occupies an angle between 70° and 90° to the first longitudinal direction of the ilium screw.

36. Method for performing a triangular iliosacral osteosynthesis using a bone anchor having an ilium screw having a first longitudinal direction and an iliosacral screw having a second longitudinal direction, wherein the ilium screw, in a thread-free portion, has an elongated through-opening formed transversely to the first longitudinal direction, and the iliosacral screw has such a smaller outer diameter in relation to the ilium screw that the iliosacral screw can be guided through said through-opening and can be screwed proceeding from the ilium into the sacrum, through the ilium screw, wherein the ilium screw has a distal threaded portion having a distal core diameter and a distal nominal diameter of the thread and a proximal threaded portion having a proximal core diameter and a proximal nominal diameter of the thread, and wherein the thread-free portion is arranged between the distal and the proximal threaded portion, wherein the proximal nominal diameter is greater than an outer diameter of the thread-free portion and the outer diameter of the thread-free portion is greater than the distal nominal diameter, and wherein a sleeve element having an inner diameter and a shape complementary to a shape of the elongated through-opening and made of a polymer material is inserted into the through-opening and is then held in the through-opening frictionally and additionally in a form-fitting manner relative to at least one direction, wherein the inner dimension of the sleeve element orthogonally to the first longitudinal direction is smaller than a nominal diameter of a thread of the iliosacral screw, characterized in that the sleeve element has at least one projection projecting transversely to its press-in direction, by means of which a form-fit engagement of the sleeve element with the ilium screw is achieved and characterized in that a first opening is formed in the ilium of a patient to be treated for screwing in the ilium screw,
 that the ilium screw is screwed in this opening such that the through hole thereof is positioned in such a way that the iliosacral screw can be screwed in a position and orientation intended by the surgeon, and
 that the sleeve element is pressed, with its protruding projection that is transverse to its press-in direction, against the form-fit engagement with the ilium screw as a result of screwing the iliosacral screw
 that a second opening is formed which extends, at an angle transverse to the first opening, through the ilium and through the passageway of the ilium screw into the sacrum of the patient to be treated,
 that the iliosacral screw is screwed into the second opening and thereby cuts into the sleeve element, which is arranged in the through hole of the ilium screw, wherein said iliosacral screw is arranged thereby in an inclination to the first longitudinal direction of the ilium screw and to the through hole of the ilium screw as intended by the surgeon, wherein this inclination is such that it occupies an angle between 70° and 90° to the first longitudinal direction of the ilium screw.

\* \* \* \* \*